United States Patent [19]

Chomczynski

[11] Patent Number: 5,346,994

[45] Date of Patent: * Sep. 13, 1994

[54] SHELF-STABLE PRODUCT AND PROCESS FOR ISOLATING RNA, DNA AND PROTEINS

[76] Inventor: Piotr Chomczynski, 778 Avon Fields La., Cincinnati, Ohio 45229

[*] Notice: The portion of the term of this patent subsequent to Jun. 27, 2006 has been disclaimed.

[21] Appl. No.: 826,984

[22] Filed: Jan. 28, 1992

[51] Int. Cl.$^5$ ............................................. C07H 21/02
[52] U.S. Cl. ................................ 530/419; 536/25.4; 536/25.41; 935/19; 935/20
[58] Field of Search ................... 536/27, 28, 29, 25.4, 536/25.41; 530/419; 935/20, 19

[56] References Cited

U.S. PATENT DOCUMENTS

| | | | |
|---|---|---|---|
| 4,843,155 | 6/1989 | Chomczynski | 536/27 |
| 5,010,183 | 4/1991 | Macfarlane | 536/27 |
| 5,128,247 | 7/1992 | Koller | 536/28 |
| 5,130,423 | 7/1992 | Van Ness et al. | 536/27 |
| 5,234,809 | 8/1993 | Boom et al. | 536/25.4 |

OTHER PUBLICATIONS

Coombs, L. M., Pigott, D., Proctor, A., Eydmann, M., Denner, J. and Knowles, M. A. "Simultaneous Isolation of DNA, RNA, and Antigenic Protein Exhibiting Kinase Activity from Small Tumor Samples Using Guanidine Isothiocyanate", Anal. Biochem. 188, 338–343 (1990).

Sela, M., Anfinsen, C. B. & Harrington, W. F. "The Correlation of Ribonuclease Activity With Specific Aspects of Tertiary Structure", Biochem. Biophys. Acta 26, 506–511 (1957).

Cox, R. A. "The Use of Guanidinium Chloride in the Isolation of Nucleic Acids", Methods in Enzymology 12(B):120–129 (1968).

Nicolaides, N. C. & Stoeckert, Jr., C. J. "A Simple, Efficient Method for the Separate Isolation of RNA and DNA from the Same Cells", Biotechniques 8, 154–156 (1990).

Raha, S., Merante, F., Proteau, G. and Reed, J. K. "Simultaneous Isolation of Total Cellular RNA and DNA from Tissue Culture Cells Using Phenol and Lithium Chloride", Gene Anal. Techn. 7, 173–177 (1990).

Chan, V. T. W., Fleming, K. A. & McGee, J. O'D. "Simultaneous Extraction from Clinical Biopsies of High–Molecular–Weight DNA and RNA: Comparative Characterization by Biotinylated and $^{32}$P–Labeled Probes on Southern and Northern Blots", Anal. Biochem. 168, 16–24 (1988).

Attardi, B. & Miklos, J. "Rapid Stimulatory Effect of Activin-A on Messenger RNA Encoding the Follicle-Stimulating Hormone Beta–Subunit in Rat Pituitary Cell Cultures", Molec. Endocrin. 4, 721–726 (1990).

Attardi, B. & Fitzgerald, T. "Effects of Progesterone on the Estradiol-Induced Follicle-Stimulating Hormone (FSH) Surge and FSH Beta Messenger Ribonucleic Acid in the Rat", Endocrinology 126, 2281–2287 (1990).

Primary Examiner—Ronald W. Griffin
Attorney, Agent, or Firm—Wood, Herron & Evans

[57] ABSTRACT

Shelf-stable solvent solutions and methods for simultaneously isolating RNA, DNA and proteins from biological samples are disclosed. The solvent solutions include phenol and a guanidinium compound, preferably at a concentration below about 2M, which is effective in isolating substantially pure and undegraded RNA, substantially pure and undegraded DNA, and proteins from the same biological sample.

30 Claims, 1 Drawing Sheet

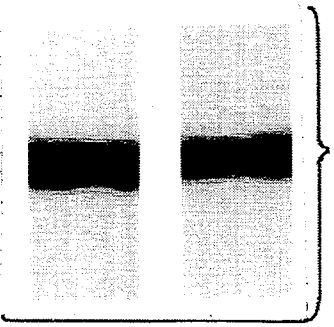

SHELF-STABLE PRODUCT AND PROCESS FOR ISOLATING RNA, DNA AND PROTEINS

FIELD OF THE INVENTION

The present invention relates to a shelf-stable solvent solution and method for simultaneously isolating RNA, DNA and proteins from biological samples.

BACKGROUND OF THE INVENTION

The extensive research and development taking place in the rapidly growing fields of molecular biology and biotechnology has increased the demand for ribonucleic acid (RNA), deoxyribonucleic acid (DNA), and proteins which can be used in experimental work and/or commercial production. All biological tissue contains RNA, DNA and proteins; however, for many clinical and research applications, it is necessary to isolate and characterize these components from tissue and cell cultures. For example, RNA and DNA isolation is necessary for molecular cloning of genes which are important in the medical and agricultural fields (e.g., insulin, growth hormone genes, and genes responsible for increased plant productivity). In addition, isolation and characterization of RNA, DNA and proteins is necessary for the early detection of molecular defects in the human genome, and for gene expression studies. In many contexts it is necessary or desirable to isolate the RNA, DNA and proteins from the same biological sample. This is extremely difficult, if not impossible, when the tissue sample size is very small, for example in biopsies, and cannot be divided and used in separate isolation techniques for each component.

There are a variety of known techniques for isolating RNA from biological tissue. For example, my earlier U.S. Pat. No. 4,843,155, the content of which is expressly incorporated herein by reference, discloses an efficient product and process for isolating RNA from biological tissue samples. Utilizing the product and process of the '155 patent, RNA can be isolated in about four hours. The '155 patent refers to and describes several other known techniques for isolating RNA, each of which has specific drawbacks. Additionally, neither the process of the '155 patent, nor the other processes referred to therein are directed to simultaneously isolating RNA, DNA, and proteins from the same tissue sample.

Other techniques are known for the simultaneous isolation of RNA and DNA. For example, U.S. Pat. No. 5,010,183 discloses a process for purifying DNA and RNA from a variety of sources, including cells, cell lysates, viruses, tissues, blood and other body fluids, employing a cationic detergent to complex with the nucleic acids. Additional protocols for simultaneous isolation of RNA and DNA are described in the following articles: Chan, V. T.-W., et al.: *Anal. Biochem.*, 168, 16–24 (1988); Nicolaides, N. C., et al.: *BioTechniques*, Vol. 8, No. 2, 154–156 (1990); and Raha, S., et al.: *Gene Anal. Techn.* (7), 173–177 (1990). Each of the described protocols extract RNA and DNA using an extraction solution containing detergents (e.g., NONIDET P-40, sodium lauryl sulfate, and sodium lauryl sarcosine) and phenol supplemented with RNase inhibitors.

A procedure for simultaneously isolating DNA, RNA and protein from the same biological sample is described in Coombs, L. M., et al.: *Anal. Biochem.*, 188, 338–343 (1990). This method is a modification of the Chirgwin et al. method referred to in my U.S. Pat. No. 4,843,155. In summary, this method is performed as follows: cell or tissue samples are homogenized in 4M guanidinium. The homogenate is overlayered on a cesium chloride (CsCl) gradient. Following centrifugation for 18 hours at 110,000–150,000 g, the top guanidinium phase contains proteins, the upper layer of CsCl contains DNA, and RNA collects at the bottom of the ultracentrifuge tube. Purification of the RNA, DNA and protein fractions collected from the cesium chloride gradient is completed in the next 12–24 hours. This method is disadvantageous because it is extremely time consuming (on the order of 2–3 days to complete) and because it requires an ultracentrifuge, which is an expensive piece of equipment that can process only a limited number and size of samples simultaneously.

Thus, there is a definite need for an efficient and accurate method for the simultaneous isolation of RNA, DNA and proteins from the same biological sample.

SUMMARY OF THE INVENTION

The present invention is directed to a shelf-stable solvent solution and a process for simultaneously isolating RNA, DNA and proteins from biological samples. The solvent solution and process provide fast, effective and accurate simultaneous isolation or extraction of substantially pure, substantially undegraded RNA, substantially pure, substantially undegraded DNA, and proteins from the same biological sample. As used herein, the term "isolated" is intended to mean that the particular component of interest, i.e., RNA, DNA or proteins, is separated or isolated from the other components to such a degree that there is no detectable contamination by those other components, as measured utilizing standard purity test procedures. Furthermore, as used herein the term "undegraded" is intended to mean that the component of interest is not degraded to any detectable degree, as measured by standard degradation test procedures.

Generally speaking, the solvent solution of the present invention includes, in combination, an effective amount of phenol and a guanidinium compound for extracting or isolating substantially pure and undegraded RNA, substantially pure and undegraded DNA, and proteins from the same biological sample. This advantageous and surprising result is achieved in a fast, effective and accurate manner, not heretofore achieved; on the order of 1–2 hours and not requiring an ultracentrifuge. By way of comparison, my earlier U.S. Pat. No. 4,843,155 disclosed a process and a solvent solution containing phenol and a guanidinium compound at a concentration in the range of 2–5M. The solvent solution is capable of isolating substantially pure, undegraded RNA in about 3 hours, but is not intended to nor is it capable of isolating substantially pure and undegraded DNA, and proteins.

With respect to the present invention, it has been unexpectedly found that the use of an effective amount of phenol in combination with a guanidinium compound, particularly at a concentration in the range of about 0.5–2M adequately protects the RNA and DNA components from degradation, allows faster more efficient isolation of RNA, and also achieves isolation of the DNA and protein components. The novel solvent solution of the present invention is shelf stable, having a usable shelf life of about two months at room temperature and about 9–12 months at 4° C., without experiencing any significant oxidation and decomposition which renders the phenol unusable in the isolation process.

In the solvent solution of the present invention, the guanidinium compound may be an acid guanidinium or a salt thereof, including, but not limited to, guanidinium thiocyanate and guanidinium hydrochloride. The guanidinium compound serves to protect the RNA and DNA components from degradation, and serves to maintain the phenol in solution in the aqueous solvent solution. The phenol serves to extract the proteins from the aqueous phase and inhibit the action of RNase and other contaminating enzymes which cause RNA degradation.

The solvent solution of the present invention may include an additional thiocyanate component such as ammonium thiocyanate or sodium thiocyanate. This additional thiocyanate component is believed to enhance the extraction of RNA from the biological sample. Additionally, the solvent solution may include a buffering component, such as sodium acetate or sodium citrate, in an amount sufficient to maintain the pH of the solution in the range of about 4–6. Furthermore, the solvent solution may include an additional solubilizer for maintaining the phenol in solution, especially at 4° C., and to achieve or maintain the solvent as a monophase solution. One suitable solubilizer is glycerol.

In a preferred embodiment, the solvent solution of the present invention has a pH in the range of about 4–6 and includes phenol, a guanidinium compound, a thiocyanate compound and a phenol solubilizer. A preferred guanidinium compound is guanidinium thiocyanate, a preferred thiocyanate compound is ammonium thiocyanate, and a preferred phenol solubilizer is glycerol.

Utilizing the solvent solution and the method of the present invention, isolation of substantially pure, substantially undegraded RNA may be completed in about one hour. The isolated RNA is suitable for Northern analysis, isolation of messenger RNA (mRNA), and for enzymatic assays, including polymerase chain reaction (PCR), without additional purification steps. The DNA component may be isolated in about 1–1½ hours using the solvent solution and method of the present invention. A high yield of extracted DNA is achieved and the DNA, which is substantially pure and undegraded, is suitable for restriction and Southern analysis. Furthermore, the method of the present invention allows for quantitation of the DNA content in a sample taken for RNA and/or protein isolation. This may be accomplished by taking an optical density reading of the isolated DNA. Finally, proteins may be isolated in about one hour utilizing the solvent solution and method of the present invention. The isolated proteins are believed to retain their antigenic properties and have sufficient purity for Western analysis.

In a preferred embodiment, the method of the present invention comprises homogenizing a biological sample in a predetermined volume of solvent solution to form a homogenate. Thereafter, a water-insoluble organic solvent, such as chloroform, is added to the homogenate and the homogenate is shaken and sedimented to form a mixture consisting of an aqueous phase containing substantially pure, substantially undegraded RNA, an organic phase containing proteins, and an interphase containing substantially pure, substantially undegraded DNA. The RNA is precipitated from the aqueous phase by the addition of a lower alcohol thereto and the precipitated RNA is recovered by sedimentation. The proteins in the organic phase are precipitated by the addition of a lower alcohol thereto and recovered by sedimentation. Finally, the DNA is recovered from the interphase by washing the interphase with a predetermined amount of the solvent solution, sedimentation of the DNA and removal of any phenol and salt contamination from the DNA.

In an alternative embodiment, subsequent to homogenation and sedimentation, both the organic phase and the interphase are extracted with water and the DNA is precipitated from the interphase by the addition of cesium chloride, sodium citrate solution and a lower alcohol. The resulting mixture is centrifuged and the sedimented DNA is recovered. In this embodiment, the RNA is recovered from the aqueous phase and the proteins are recovered from the organic phase in the manner described in the previous embodiment.

In another alternative embodiment, subsequent to homogenation of the biological sample in the solvent solution of the present invention, substantially pure, substantially undegraded DNA is sedimented from the homogenate since it is insoluble in the solvent solution. The sedimented DNA is then washed with a predetermined amount of the solvent solution and any phenol and/or salt contamination is removed therefrom. A water-insoluble organic solvent (such as chloroform) is added to the residual homogenate, which contains RNA and proteins, and the homogenate is shaken and sedimented to form a mixture having an aqueous phase containing substantially pure, substantially undegraded RNA and an organic phase containing proteins. As in the previous embodiments, the RNA is precipitated from the aqueous phase by the addition of a lower alcohol and recovered by sedimentation. Likewise, the proteins are precipitated from the organic phase by the addition of a lower alcohol and recovered by sedimentation.

BRIEF DESCRIPTION OF THE FIGURES

FIG. 1A shows the results of total RNA analysis by Northern blotting;

FIG. 1B shows the results of DNA analysis by Southern blotting; and

FIG. 1C shows the results of protein analysis by Western blotting.

DETAILED DESCRIPTION OF THE INVENTION

In a preferred embodiment, the solvent solution of the present invention, which is shelf-stable, comprises guanidinium thiocyanate at a concentration in the range of about 0.5–2M, based on the total volume of the solvent solution; ammonium thiocyanate at a concentration in the range of about 0.1–0.6M, based on the total volume of the solvent solution; a buffer (preferably sodium acetate) in an amount sufficient to maintain the pH of the solvent solution in the range of about 4–6; glycerol in the amount of about 3%–10% by volume based on the total volume of the solvent solution; and phenol in the amount of about 30%–50% by volume based on the total volume of the solvent solution.

In a more preferred embodiment of the solvent solution, the concentration of guanidinium thiocyanate is preferably about 0.8M, the concentration of ammonium thiocyanate is preferably about 0.4M, the sodium acetate buffer is present in a concentration of about 0.1M, based on the total volume of the solvent solution, whereby the solution has a pH of about 5.0. Additionally, the solvent solution comprises about 5% by volume glycerol and about 38% by volume phenol.

The following examples are illustratives of alternative embodiments of the method of the present invention.

EXAMPLE 1

100 mg of a tissue sample is homogenized in 2 ml of the preferred solvent solution described hereinabove. Thereafter, 0.4 ml of chloroform is added to the homogenate and the mixture is shaken and sedimented at 12,000 g for ten minutes. Following sedimentation, the mixture forms an aqueous phase containing substantially pure, substantially undegraded RNA, an organic phase containing proteins, and an interphase containing substantially pure, substantially undegraded DNA. The aqueous phase is collected and combined with 2ml of isopropanol and centrifuged at 12,000 g for ten minutes. The sediment containing total RNA is washed with 2 ml of 75% ethanol, centrifuged at 8000 g for six minutes, and dissolved in water. The isolation of RNA as described takes about one hour.

The DNA is isolated using one of three alternative protocols. In one embodiment, both the organic phase and the interphase are extracted with 1 ml of water. Then, the DNA is precipitated from the interphase by the addition of 100 ul of 4.5M CsCl, 0.5M sodium citrate solution and 2 ml ethanol. The resulting mixture is centrifuged and the sedimented DNA is washed four times with 2 ml of 75% ethanol and once with 2 ml of water.

In an alternative embodiment, the interphase is removed from the organic phase, placed in a new tube and washed with 0.5 ml of the solvent solution. Any phenol and/or salt contamination of the DNA is removed by successive washes in 75% ethanol, 30% ethanol/2.8M NaBr solution, and finally with 75% ethanol.

In another alternative embodiment, DNA is sedimented from the initial homogenate, prior to the addition of chloroform, since DNA is not soluble in the solvent solution. The sedimented DNA is washed with 0.5 ml of the solvent solution and purified from phenol and/or salt contamination by successive washes in 75% ethanol, 30% ethanol/2.8M NaBr solution, and finally with 75% ethanol. DNA isolation according to the above-described procedures is accomplished in about 1-1½ hours.

Proteins are precipitated from the organic phase by the addition of two volumes of isopropanol. The suspension is centrifuged and the protein precipitate is washed two times with ethanol and dissolved in 0.5% sodium dodecyl sulphate solution. The protein isolation is completed in about one hour.

EXAMPLE 2

In another specific example of the method of the present invention, 152 mg of rat mammary gland is homogenized in a teflon-glass homogenizer with 3 ml of the preferred solvent solution described hereinabove. Following homogenation, 0.6 ml of chloroform is added to the homogenate. The mixture is shaken and centrifuged at 12,000 g for ten minutes at 4° C. After centrifugation, the homogenate forms an aqueous phase, interphase, and organic phase.

RNA Isolation

The aqueous phase is transferred into a new tube, and RNA is precipitated by the addition of 1.5 ml of isopropanol and centrifugation at 8000 g for eight minutes at 4° C. The sediment containing total RNA is washed with 3 ml of 75% ethanol, centrifuged at 8000 g for five minutes, and dissolved in water. The yield of total RNA is 0.62 mg with no detectable DNA or protein contamination, as tested by the diphenylamine (Burton, K.: Biochem. J., 62:315-322 (1956)) and Folin (Peterson, G. L.: Methods in Enzymology, 91:95-98 (1983)) reagents, respectively.

DNA Isolation

The organic phase and interphase are extracted with 1.5 ml of water and the mixture is centrifuged at 3000 g for five minutes. The aqueous phase is removed and DNA is precipitated therefrom by the successive addition of 150 ul of 4.5M CsCl, 0.5M sodium citrate solution, and 1.5 ml ethanol. The mixture is shaken for 15 seconds and centrifuged at 3000 g for three minutes. The resulting supernatant, containing the organic phase, is set aside for protein isolation. The pelleted DNA is washed four times by vortexing with 3 ml of 75% ethanol and centrifugation at 3000 g for three minutes. The DNA pellet is then suspended in 3 ml of 100% ethanol, centrifuged at 3000 g for three minutes and dissolved in water. The DNA yield is 0.41 mg with no detectable protein contamination, as tested by the Folin reagent.

In separate assays, the purity of the isolated RNA and DNA is tested using $^3$H RNA and $^{32}$P DNA as contaminating agents. No radioactive DNA is detected in the RNA preparation and no radioactive RNA is detected in the DNA preparation.

Protein Isolation

The organic phase set aside during the DNA isolation step is mixed with 6 ml of isopropanol. The mixture is held at room temperature for five minutes and the precipitated proteins are centrifuged at 10,000 g for ten minutes. The protein pellet is suspended in 3 ml of ethanol by vortexing, then held at room temperature for five minutes and thereafter centrifuged at 10,000 g for ten minutes. This washing/centrifuging process is repeated three times. Following the final ethanol wash, the protein pellet is briefly air-dried (ten minutes) and dissolved in water. The protein yield is 6.3 mg.

The quality of the RNA, DNA and protein isolated in this Example is tested using standard Northern, Southern and Western analyses, respectively. The Northern, Southern and Western analyses are performed according to the standard protocols described in Ausbell, F. M. et al. (Eds.): Current Protocols in Molecular Biology, Wiley Interscience, New York (1990), which are incorporated herein by reference.

In the Northern analysis, 5 ug of the total RNA isolated is electrophoresed in 1% agarose-formaldehyde gel, transferred to a "Nytran" membrane and hybridized with nick-translated α-lactalbumin cDNA. It is believed that the presence of an undegraded band of α-lactalbumin mRNA, as shown in FIG. 1A, exemplifies that the isolated total RNA is undegraded.

In the Southern analysis, 5 ug of the isolated DNA is digested by EcoR1 restrictase, electrophoresed in 1% agarose gel, transferred to a "Nytran" membrane and hybridized with nick-translated α-lactalbumin cDNA. It is believed that the presence of an undegraded band of EcoR1 fragment of α-lactalbumin gene, as shown in FIG. 1B, exemplifies that the isolated DNA is undegraded.

In the Western analysis, 50ug of the isolated protein is electrophoresed in 10% acrylamide-SDS gel and electrotransferred to a nitrocellulose membrane. The presence of α-lactalbumin is detected using rabbit, anti-rat α-lactalbumin antibody and a peroxidase-conjugated anti-rabbit IgG. It is believed that the presence of a specific protein in the isolate is exemplified by the detection of α-lactalbumin, as shown in FIG. 1C.

The scope of the present invention is not intended to be limited by the specific examples provided herein, but is to be accorded a scope commensurate with the appended claims.

What is claimed is:

1. A solvent solution comprising: effective amounts of phenol, a guanidinium compound and a thiocyanate compound selected from the group consisting of ammonium thiocyanate and sodium thiocyanate for extracting substantially pure and undegraded RNA, substantially pure and undegraded DNA, and proteins from biological tissue.

2. The solvent solution of claim 1, said thiocyanate compound being present at a concentration in the range of about 0.1–0.6M, based on the total volume of said solvent solution.

3. A solvent solution comprising: effective amounts of phenol, a guanidinium compound and sodium acetate present at a concentration of about 0.1M, based on the total volume of said solvent solution, said solvent solution having a pH of about 5.0 for extracting substantially pure and undegraded RNA, substantially pure and undegraded DNA, and proteins from biological tissue.

4. A solvent solution comprising: effective amounts of phenol, a guanidium compound and a phenol solubilizer for extracting substantially pure and undegraded RNA, substantially pure and undegraded DNA, and proteins from biological tissue.

5. The solvent solution of claim 4, said phenol solubilizer being glycerol.

6. The solvent solution of claim 5, said glycerol being present in the range of about 3%–10% by volume of said solvent solution, based on the total volume of said solvent solution.

7. The solvent solution of claim 6, said phenol being present in the range of about 30%–50% by volume of said solvent solution, based on the total volume of said solvent solution.

8. A solvent solution for extracting substantially pure RNA, DNA and proteins from biological tissue, said solvent solution comprising:
(a) guanidinium thiocyanate at a concentration in the range of about 0.5–2M, based on the total volume of said solvent solution;
(b) a buffer in an amount sufficient to maintain the pH of said solvent solution in the range of about 4–6;
(c) phenol in the amount of about 30%–50% by volume based on the total volume of said solvent solution; and
(d) a phenol solubilizer in the amount of about 3%–10% by volume based on the total volume of said solvent solution.

9. The solvent solution of claim 8 further comprising ammonium thiocyanate at a concentration in the range of about 0.1–0.6M, based on the total volume of said solvent solution.

10. The solvent solution of claim 8, said phenol solubilizer being glycerol.

11. The solvent solution of claim 8, said guanidinium thiocyanate concentration being about 0.8M.

12. The solvent solution of claim 9, said ammonium thiocyanate concentration being about 0.4M.

13. The solvent solution of claim 8, said buffer being sodium acetate.

14. The solvent solution of claim 13, said sodium acetate being present at a concentration of about 0.1M, based on the total volume of said solvent solution, said solvent solution having a pH of about 5.0.

15. The solvent solution of claim 10, said glycerol comprising about 5% by volume of said solvent solution.

16. The solvent solution of claim 8, said phenol comprising about 38% by volume of said solvent solution.

17. A method of isolating substantially pure RNA, DNA and proteins from biological tissue, comprising the steps of:
(a) homogenizing a tissue sample in the solvent solution of claim 1 to form a homogenate;
(b) adding a water-insoluble organic solvent to said homogenate and sedimenting to form a mixture consisting of an aqueous phase containing substantially pure, undegraded RNA, an organic phase containing proteins, and an interphase containing substantially pure, undegraded DNA;
(c) precipitating RNA from the aqueous phase by the addition of a lower alcohol thereto and recovering the precipitated RNA by sedimentation;
(d) precipitating proteins from the organic phase by the addition of a lower alcohol thereto and recovering the precipitated proteins by sedimentation; and
(e) recovering DNA from the interphase by washing the interphase with a predetermined amount of said solvent solution, sedimentation of the DNA and removal of any phenol and salt contamination from the DNA.

18. The method of claim 17 wherein said water-insoluble organic solvent added to said homogenate is chloroform.

19. The method of claim 17 wherein the lower alcohol added to the aqueous phase is isopropanol.

20. The method of claim 17 wherein the lower alcohol added to the organic phase is isopropanol.

21. A method of isolating substantially pure RNA, DNA and proteins from biological tissue, comprising the steps of:
(a) homogenizing a tissue sample in the solvent solution of claim 1 to form a homogenate;
(b) adding a water-insoluble organic solvent to said homogenate and sedimenting to form a mixture consisting of an aqueous phase containing substantially pure, undegraded RNA, an organic phase containing proteins, and an interphase containing substantially pure, undegraded DNA;
(c) precipitating RNA from the aqueous phase by the addition of a lower alcohol thereto and recovering the precipitated RNA by sedimentation;
(d) extracting the organic phase and interphase with water;
(e) precipitating proteins from the organic phase by the addition of a lower alcohol thereto and recovering the precipitated proteins by sedimentation; and
(f) precipitating DNA from the interphase by the addition of CsCl, sodium citrate solution and a lower alcohol thereto and recovering the precipitated DNA by sedimentation.

22. The method of claim 21 wherein said water-insoluble organic solvent added to said homogenate is chloroform.

23. The method of claim 21 wherein the lower alcohol added to the aqueous phase is isopropanol.

24. The method of claim 21 wherein the lower alcohol added to the organic phase is isopropanol.

25. The method of claim 21 wherein the lower alcohol added to the interphase is ethanol.

26. A method of isolating substantially pure RNA, DNA and proteins from biological tissue, comprising the steps of:
   (a) homogenizing a tissue sample in the solvent solution of claim 1 to form a homogenate;
   (b) sedimenting substantially pure, undegraded DNA from said homogenate, washing the sedimented DNA with an amount of said solvent solution, and removing any phenol and salt contamination from the DNA;
   (c) adding a water-insoluble organic solvent to the residual homogenate subsequent to said DNA sedimenting step, and thereafter sedimenting to form a mixture having an aqueous phase containing substantially pure, undegraded RNA and an organic phase containing proteins;
   (d) precipitating RNA from the aqueous phase by the addition of a lower alcohol thereto and recovering the precipitated RNA by sedimentation;
   (e) precipitating proteins from the organic phase by the addition of a lower alcohol thereto and recovering the precipitated proteins by sedimentation.

27. The method of claim 26 wherein said water-insoluble organic solvent added to said residual homogenate is chloroform.

28. The method of claim 26 wherein said lower alcohol added to the aqueous phase is isopropanol.

29. The method of claim 26 wherein said lower alcohol added to the organic phase is isopropanol.

30. A method of isolating substantially pure RNA, DNA and proteins from biological tissue, comprising the steps of:
   (a) precipitating RNA from an aqueous phase obtained from a mixture consisting of an aqueous phase containing substantially pure, undegraded RNA, an organic phase containing proteins, and an interphase containing substantially pure, undegraded DNA, said mixture formed by adding a water-insoluble organic solvent to a homogenate and sedimenting, said homogenate formed by homogenizing a tissue sample in a solvent solution comprising effective amounts of phenol and a guanidinium compound for extracting substantially pure and undegraded RNA, substantially pure and undegraded DNA, and proteins from biological tissue, by the addition of a lower alcohol thereto and recovering the precipitated RNA by sedimentation;
   (b) precipitating proteins from an organic phase obtained from a mixture consisting of an aqueous phase containing substantially pure, undegraded RNA, an organic phase containing proteins, and an interphase containing substantially pure, undegraded DNA, said mixture formed by adding a water-insoluble organic solvent to a homogenate and sedimenting, said homogenate formed by homogenizing a tissue sample in a solvent solution comprising effective amounts of phenol and a guanidinium compound for extracting substantially pure and undegraded RNA, substantially pure and undegraded DNA, and proteins from biological tissue, by the addition of a lower alcohol thereto and recovering the precipitated proteins by sedimentation; and
   (c) recovering DNA from an interphase obtained from a mixture consisting of an aqueous phase containing substantially pure, undegraded RNA, an organic phase containing proteins, and an interphase containing substantially pure, undegraded DNA, said mixture formed by adding a water-insoluble organic solvent to a homogenate and sedimenting, said homogenate formed by homogenizing a tissue sample in a solvent solution comprising effective amounts of phenol and a guanidinium compound for extracting substantially pure and undegraded RNA, substantially pure and undegraded DNA, and proteins from biological tissue, by washing the interphase with a predetermined amount of said solvent solution, sedimentation of the DNA and removal of any phenol and salt contamination from the DNA.

* * * * *

UNITED STATES PATENT AND TRADEMARK OFFICE
CERTIFICATE OF CORRECTION

PATENT NO. : 5,346,994
DATED : September 13, 1994
INVENTOR(S) : Piotr Chomczynski It is certified that error appears in the above-indentified patent and that said Letters Patent is hereby corrected as shown below:

At column 5, line 26, "2ml" should be --1ml--.

Signed and Sealed this

Twenty-seventh Day of December, 1994

Attest:

BRUCE LEHMAN

Attesting Officer     Commissioner of Patents and Trademarks